United States Patent
Vahala

(10) Patent No.: US 10,265,016 B2
(45) Date of Patent: Apr. 23, 2019

(54) HYPERTHERMIA FOR DIAGNOSTIC IMAGING

(71) Applicant: KONINKLIJKE PHILIPS N.V., Eindhoven (NL)

(72) Inventor: Erkki Tapani Vahala, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 590 days.

(21) Appl. No.: 14/767,948

(22) PCT Filed: Feb. 19, 2014

(86) PCT No.: PCT/EP2014/053198
§ 371 (c)(1),
(2) Date: Aug. 14, 2015

(87) PCT Pub. No.: WO2014/128147
PCT Pub. Date: Aug. 28, 2014

(65) Prior Publication Data
US 2015/0374287 A1   Dec. 31, 2015

(30) Foreign Application Priority Data

Feb. 22, 2013   (EP) .................................. 13156374

(51) Int. Cl.
*A61B 5/00* (2006.01)
*A61N 7/02* (2006.01)
(Continued)

(52) U.S. Cl.
CPC ............ *A61B 5/4836* (2013.01); *A61B 5/015* (2013.01); *A61B 5/055* (2013.01); *A61B 5/743* (2013.01);
(Continued)

(58) Field of Classification Search
None
See application file for complete search history.

(56) References Cited

U.S. PATENT DOCUMENTS 5,284,144 A * 2/1994 Delannoy ............... A61B 5/055
324/315
5,722,411 A   3/1998 Suzuki et al.
(Continued)

FOREIGN PATENT DOCUMENTS

EP   2500740 A1   9/2012
WO   02082995 A1   10/2002
(Continued)

*Primary Examiner* — Tse W Chen
*Assistant Examiner* — Joanne M Hoffman

(57) ABSTRACT

A diagnostic imaging system (100) includes a magnetic resonance (MR) imaging system (110) for providing an image representation of at least a portion of a subject of interest (120), a hyperthermia device (111) for locally heating a target zone within the portion of the subject of interest (120), and one or more processors for controlling the MR imaging system (110) and the hyperthermia device (111). Correlating image representations obtained at different temperatures of the target zone provides information on temperature dependent changes of the metabolism of the subject of interest (120). A treatment module (146) applies a treatment to the subject of interest (120) for destroying cells within the target zone. The one or more processors control the treatment module (146) for applying the treatment based on diagnostic image representations obtained by the diagnostic imaging system (100). Changes of the metabolism of the subject of interest are evaluated to direct a treatment to such areas, where the cells have not yet been destroyed.

1 Claim, 3 Drawing Sheets

(51) Int. Cl.
*A61B 5/01* (2006.01)
*A61B 5/055* (2006.01)
*G01R 33/48* (2006.01)
*A61N 5/10* (2006.01)
*A61B 18/14* (2006.01)
*A61N 1/40* (2006.01)
*G06T 7/00* (2017.01)
*A61B 18/00* (2006.01)
*A61N 7/00* (2006.01)
*A61B 90/00* (2016.01)

(52) U.S. Cl.
CPC .............. *A61B 18/14* (2013.01); *A61N 1/403* (2013.01); *A61N 5/1039* (2013.01); *A61N 7/02* (2013.01); *G01R 33/4814* (2013.01); *G06T 7/0012* (2013.01); *A61B 2018/00738* (2013.01); *A61B 2018/00791* (2013.01); *A61B 2090/374* (2016.02); *A61N 2005/1055* (2013.01); *A61N 2007/0082* (2013.01); *G06T 2207/10096* (2013.01); *G06T 2207/30004* (2013.01); *G06T 2207/30196* (2013.01)

(56) References Cited

U.S. PATENT DOCUMENTS

| | | | | |
|---|---|---|---|---|
| 6,128,522 | A * | 10/2000 | Acker | A61B 5/055 335/298 |
| 6,368,275 | B1 * | 4/2002 | Sliwa | A61B 5/0031 600/302 |
| 6,522,142 | B1 * | 2/2003 | Freundlich | A61B 5/01 324/309 |
| 8,139,714 | B1 * | 3/2012 | Sahadevan | A61N 5/025 378/63 |
| 2002/0151786 | A1 | 10/2002 | Shukla et al. | |
| 2004/0101969 | A1 * | 5/2004 | Viglianti | A61B 5/055 436/173 |
| 2005/0186241 | A1 * | 8/2005 | Boyle | A61B 5/076 424/423 |
| 2005/0201516 | A1 * | 9/2005 | Ruchala | A61N 5/103 378/65 |
| 2005/0226377 | A1 * | 10/2005 | Wong | A61N 5/10 378/65 |
| 2007/0197904 | A1 * | 8/2007 | Viglianti | A61B 5/055 600/420 |
| 2008/0086050 | A1 * | 4/2008 | Misic | A61B 5/055 600/411 |
| 2009/0088623 | A1 * | 4/2009 | Vortman | A61B 5/416 600/411 |
| 2009/0221902 | A1 * | 9/2009 | Myhr | A61M 37/0092 600/411 |
| 2010/0106005 | A1 * | 4/2010 | Karczmar | A61N 5/1049 600/411 |
| 2010/0185080 | A1 * | 7/2010 | Myhr | A61N 5/02 600/411 |
| 2011/0137147 | A1 * | 6/2011 | Skliar | A61N 7/02 600/411 |
| 2011/0306870 | A1 * | 12/2011 | Kuhn | A61B 5/0515 600/411 |
| 2012/0295274 | A1 * | 11/2012 | Akahoshi | A61K 49/16 435/7.1 |
| 2013/0035921 | A1 * | 2/2013 | Rodriguez-Ponce | A61B 5/015 703/11 |
| 2013/0096595 | A1 * | 4/2013 | Myhr | A61N 1/403 606/169 |
| 2014/0266198 | A1 * | 9/2014 | Tadic | G01R 33/387 324/309 |

FOREIGN PATENT DOCUMENTS

| | | |
|---|---|---|
| WO | 2007014093 A2 | 2/2007 |
| WO | 2008011725 A1 | 1/2008 |
| WO | 2010094777 A1 | 8/2010 |

* cited by examiner

HYPERTHERMIA FOR DIAGNOSTIC IMAGING

CROSS-REFERENCE TO PRIOR APPLICATIONS

This application is the U.S. National Phase application under 35 U.S.C. § 371 of International Application No. PCT/EP2014/053198, filed on Feb. 19, 2014, which claims the benefit of EP Patent Application No. EP13156374.4, filed on Feb. 22, 2013. These applications are hereby incorporated by reference herein.

FIELD OF THE INVENTION

The invention relates to the field of diagnostic imaging, in particular magnetic resonance imaging, and treatments for destroying cells within a subject of interest.

BACKGROUND OF THE INVENTION

Diagnostic imaging like magnetic resonance imaging (MRI) is becoming a more important issue in the area of therapy. In particular, diagnostic imaging is used in the area of cancer treatments to plan an efficient treatment of cancerous tissues in an area of interest of the subject of interest, as described e.g. in WO 02/082995 A1. As described therein, a magnetic resonance (MR) apparatus is used to plan a treatment regimen using a linear accelerator (linac). The features of slice width selection and depth selection are used to better ascertain where a medial malignancy is within a subject of interest, which is an animate being, e.g. a human being or an animal. A conversion algorithm translates the linac input into an imaging region for a magnetic resonance sequence that images the malignancy. Along each planned treatment trajectory radiation and MR projection images are superimposed to delineate the malignancy clearly for beam aiming and collimation adjustments. This enables a reliable planning of the treatment.

Nevertheless, the effectiveness of the treatment is not known during the irradiation treatment. This also applies to all kinds of treatments, in particular cancer treatments, where cells within the subject of interest are destroyed. Similarly, the cell death due to chemotherapy or tissue necrosis due to heating is difficult to measure. Current MR imaging and MR spectroscopy, which rely on blood oxygen level, are sensitive to patient movement and errors from signal changes due to the therapy.

U.S. Pat. No. 528,411 describes a hyperthermia/MRI probe which is utilized to monitor temperatures within a heating zone.

U.S. Pat. No. 5,722,411 describes an ultrasound apparatus, which can be used for thermal treatment. U.S. Pat. No. 5,722,411 mentions a method in which imaging for a treatment effect check is performed.

SUMMARY OF THE INVENTION

It is an object of the invention to provide means and methods for improved diagnostic imaging and for improved treatment for destroying cells within the target zone of a subject of interest.

In one aspect of the present invention, the object is achieved by a diagnostic imaging system, comprising a magnetic resonance imaging system for providing an image representation of at least a portion of a subject of interest positioned in an examination space, a hyperthermia device for locally heating a target zone within the portion of the subject of interest, and a control unit for controlling the MR imaging system and the hyperthermia device, wherein the diagnostic imaging system is adapted to provide a diagnostic image representation of the portion of the subject of interest by correlating image representations obtained at different temperatures of the target zone, wherein the diagnostic image representation comprises information on temperature dependent changes of the metabolism of the subject of interest.

In a further aspect of the present invention, the object is achieved by a treatment system, in particular an oncological treatment system, comprising a diagnostic imaging system as described above, a treatment module for applying a treatment to the subject of interest for destroying cells within the target zone, and a control module for controlling the treatment module for applying the treatment based on diagnostic image representations obtained by the diagnostic imaging system.

In a further aspect of the present invention, the object is achieved by a method for providing a diagnostic image representation of a portion of a subject of interest, comprising the steps of providing an image representation of at least a portion of a subject of interest positioned in an examination space, whereby a target zone of the portion of subject of interest has a first temperature, locally heating the target zone, providing a further image representation of the portion of the subject of interest positioned in an examination space, whereby the target zone has a second temperature, correlating the obtained image representations with the target zone having the first and the second temperature, and providing a diagnostic image representation of the portion of the subject of interest with the correlated image representations, wherein the diagnostic image representation comprises information on temperature dependent changes of the metabolism of the subject of interest.

In a further aspect of the present invention, the object is achieved by a method for treatment, in particular for oncological treatment, of a subject of interest, comprising the steps of applying a treatment dose for destroying cells within the target zone of the subject of interest, providing a diagnostic image representation of a portion of a subject of interest covering the target zone according to the above method, and applying a further treatment dose for destroying cells within the target zone of the subject of interest based on the diagnostic image representation.

In a still further aspect of the present invention, the object is achieved by a software package for upgrading a magnetic resonance (MR) imaging system, whereby the software package contains instructions for controlling the MR imaging system according to the above method.

Accordingly, changes of the metabolism of the subject of interest, which is an animate being, e.g. a human being or an animal, can be evaluated using the MR imaging system. This information can be used to direct a treatment to such areas, where the cells have not yet been destroyed as desired. Such metabolism changes can be identified based on oxygenation, e.g., by a blood oxygen level dependent (BOLD) image representations, which can be evaluated by magnetic resonance (MR) scans. Another possibility of identifying metabolism changes is MR spectroscopy, which enables the detection of the amount of metabolic activity. Also, Perfusion and/or diffusion imaging can be used to detect an altered flow within tissues in the subject of interest. By comparing the difference of the above measurements between the first and the second temperature, the efficiency of the treatment can be evaluated and the further treatment can be adapted based on the metabolism changes. Areas, where the cells have already been destroyed, can be excluded from further treatments to speed up the treatment and reduce the stress and exposure for a subject of interest. In general, the temperature of the subject of interest is not part of the diagnostic image representation.

Accordingly, treatment doses can be adapted in respect to intensity and/or location. In particular, the control module can control the treatment module for applying the treatment to apply a treatment dose with an adapted intensity at an adapted location.

The first and second image representation are usually provided in a near temporal context, e.g. during a treatment with the treatment system. The image representations are preferably provided when a desired temperature is reached or the heating has been performed for a pre-defined time.

The hyperthermia device can be any kind of device for locally heating the target zone. Preferably, the hyperthermia device is adapted to direct heat to the target zone to avoid the heating of areas out of the target zone. The hyperthermia device can be provided integrally within the MRI system. Preferably, the hyperthermia device is arranged to heat the target zone of the subject of interest when positioned within the examination space. Further preferred, the hyperthermia device is positioned in or at the examination space. Nevertheless, it is also possible to provide the hyperthermia device separately, and the subject of interest is moved into the examination space of the MRI system for providing the image representations thereof and to a different location for applying heat with the hyperthermia device. Preferably, a contact gel pad is provided to facilitate transmission of heat from the ultrasound-based hyperthermia device to the target zone. In a further embodiment, the hyperthermia device is a device movable within the examination space.

The image representations, including the diagnostic image representation, can be provided in any suitable form, e.g. as visible images. Nevertheless, it is not required to provide the image representations as images, they can be provided as any kind of data achieved from an imaging system prior to generating the image. E.g. the diagnostic image representation can be generated based on data received when performing MR scans of the portion of the subject of interest. Also the diagnostic image representation can be provided in any form. E.g. the diagnostic image representation can be provided in any form suitable for the control module to automatically control the treatment module. The diagnostic image representation is preferably provided as visible image indicating the metabolism changes. The image representation can also comprise two or more kinds of representations, e.g. a visible image that enables an operator of the diagnostic imaging system and/or the treatment system to verify the metabolism activity and/or the metabolism changes, and a representation which is e.g. passed directly to the control module.

The control unit for controlling the MRI system and the hyperthermia device can be a separate control unit, or a control unit of the MRI system, which is adapted to additionally control the hyperthermia device.

In the treatment system, the treatment module can be any kind of device suitable to achieve the destruction of cells. The treatment module can be provided integrally within the MRI system. Preferably, the treatment module is arranged to destroy cells within the target zone of the subject of interest when positioned within the examination space. Further preferred, the treatment module is positioned in or at the examination space. Nevertheless, it is also possible to provide the treatment module separately, and the subject of interest is moved into the examination space of the MRI system for providing the image representations thereof and to a different location for applying treatment with the treatment module. In a further embodiment, the treatment module is a device movable within the examination space.

The control module for controlling the treatment module and the diagnostic imaging system can be a separate control module, or a control unit of the diagnostic imaging system, which is adapted to additionally control the treatment module. Furthermore, the control module can be a control unit of the MRI system, which is adapted to additionally control the treatment module and the hyperthermia device.

The first temperature generally refers to a temperature without heating the target zone, and the second temperature refers to a temperature after the target area has been heated. One temperature, usually the first temperature, refers to normal body temperature. The lower temperature, typically the body temperature, can be obtained after heating the target zone with the hyperthermia device through normal thermal conduction and perfusion. Nevertheless, the method can also be performed by first heating the target zone to the second temperature and then cooling the target zone to the first temperature for providing the further image representation. The cooling can comprise active cooling or normal thermal conduction and perfusion only.

The step of applying a treatment dose for destroying cells within the target zone refers to any kind of suitable treatment. The treatment module can directly or indirectly achieve the destruction of the cells.

The method steps of the above methods can be performed in any suitable order and are not limited to the order listed above. In the method for treatment, the steps of providing a diagnostic image representation and applying a further treatment dose can be performed repeatedly to provide a treatment with a continuous verification of the success of the treatment and a continuous adaptation to the diagnostic image representation.

The target zone refers to a 3-dimensional zone within the subject of interest, where the cells to be destroyed are located. Typically, the target zone is a zone containing cancerous cells.

According to a preferred embodiment of the diagnostic imaging system the control unit is adapted to perform a pulsed operation of the hyperthermia device and the MR imaging system to provide an image representation of the portion of the subject of interest when the hyperthermia device is inactive. Correlation errors can be reduced by an efficient modulation of the hyperthermia device and the MR imaging system. Accordingly, the operation of the MR imaging system is not limited by the operation of the hyperthermia device.

According to a preferred embodiment of the diagnostic imaging system the hyperthermia device is an ultrasonic and/or a radio-frequency (RF) irradiation device. The irradiation can be used to efficiently heat the target zone within the subject of interest directly. Heating of the subject of interest outside the target zone can be reduced.

According to a preferred embodiment the hyperthermia device is a heat source, which can be brought into contact with the subject of interest.

According to a preferred embodiment the diagnostic imaging system comprises an application module for applying a contrast agent to the subject of interest. The contrast agent can be used to improve the diagnostic image representation in respect to changes of the metabolism of the subject of interest. Contrast agents can be sensitive to heat shock proteins, oxygen concentration, radiation damage or others.

According to a preferred embodiment the diagnostic imaging system is adapted to provide a diagnostic image representation of the portion of the subject of interest including hypoxia information of the portion of the subject of interest. Cancerous cells frequently show a reduced local hypoxia. By comparing the difference between the first and second temperature signals of the target zone, the amount of hypoxia can be estimated, and the amount of treatment damage to the cells can be estimated from the temporally altered response due to the thermal stress. The hypoxia information can be fed back to dose calculations even before the treatment starts, to boost the dose on hypoxic volumes. The damage estimation can be used to optimize the amount of dose to minimize damage to healthy tissue while ensuring the effectiveness of treatment on the target zone during the irradiation or a single fraction. For example, with blood oxygen level dependent (BOLD) image representations, hypoxic tissue does not show a similar change due to different temperatures as normal tissue.

According to a preferred embodiment of the treatment system the control module is further adapted to control the hyperthermia device for locally heating the target zone within the portion of the subject of interest together with the treatment module for applying the treatment. In addition to improving location and doses of the treatment, the hyperthermia can be used to enhance the outcome of the treatment, i.e. the treatment effectiveness can be improved by hyperthermia. This is partly due to increased metabolism, altered blood-flow, and reduced local hypoxia often present in cancerous tissue. Due to the locally applied heat, cells outside the target zone are not subject to an increased destruction.

According to a preferred embodiment of the treatment system the treatment module comprises a high power linear accelerator for applying irradiation to the target zone of the subject of interest. The linear accelerator (linac) can be used to irradiate the target zone with high accuracy in respect to location and intensity, i.e. dose.

According to a preferred embodiment of the treatment system the treatment module comprises a high intensity focused ultrasound device for applying ultrasound to the target zone of the subject of interest. The high intensity focused ultrasound (HIFU) device can be used to irradiate the target zone with high accuracy in respect to location and intensity, i.e. dose. Preferably, the HIFU device can be used as hyperthermia device when controlled to heat the target area with low intensity, so that a separate hyperthermia device can be omitted.

According to a preferred embodiment of the treatment system the treatment module comprises a chemotherapy/drug release module for releasing drugs into the subject of interest. The drugs can destroy the cells, or improve the destruction of the cells when using a further treatment system as from the above treatment systems. The release module is preferably provided to release the drugs in or close to the target zone.

According to a preferred embodiment the method for providing a diagnostic image representation comprises applying a contrast agent to the subject of interest. The contrast agent can be used to improve the diagnostic image representation in respect to changes of the metabolism of the subject of interest. Contrast agents can be sensitive to heat shock proteins, oxygen concentration, radiation damage or others.

According to a preferred embodiment of the method for providing a diagnostic image representation the step of providing a diagnostic image representation of the portion of the subject of interest with the correlated image representations comprises identifying hypoxic areas within the portion of the subject of interest. Cancerous cells frequently show a reduced local hypoxia. By comparing the difference between the first and second temperature signals of the target zone, the amount of hypoxia can be estimated, and the amount of treatment damage to the cells can be estimated from the temporally altered response due to the thermal stress. The hypoxia information can be fed back to dose calculations even before the treatment starts, to boost the dose on hypoxic volumes. The damage estimation can be used to optimize the amount of dose to minimize damage to healthy tissue while ensuring the effectiveness of treatment on the target zone during the irradiation or a single fraction. For example, with blood oxygen level dependent (BOLD) image representations, hypoxic tissue does not show a similar change due to different temperatures as normal tissue.

According to a preferred embodiment of the method for treatment of a subject of interest the step of applying a treatment dose for destroying cells within the target zone of the subject of interest comprises locally heating the target zone. In addition to improving location and doses of the treatment, the hyperthermia can be used to enhance the outcome of the treatment, i.e., the treatment effectiveness can be improved by hyperthermia. This is partly due to increased metabolism, altered blood-flow, and reduced local hypoxia often present in cancerous tissue. Due to the locally applied heat, cells outside the target zone are not subject to an increased destruction.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
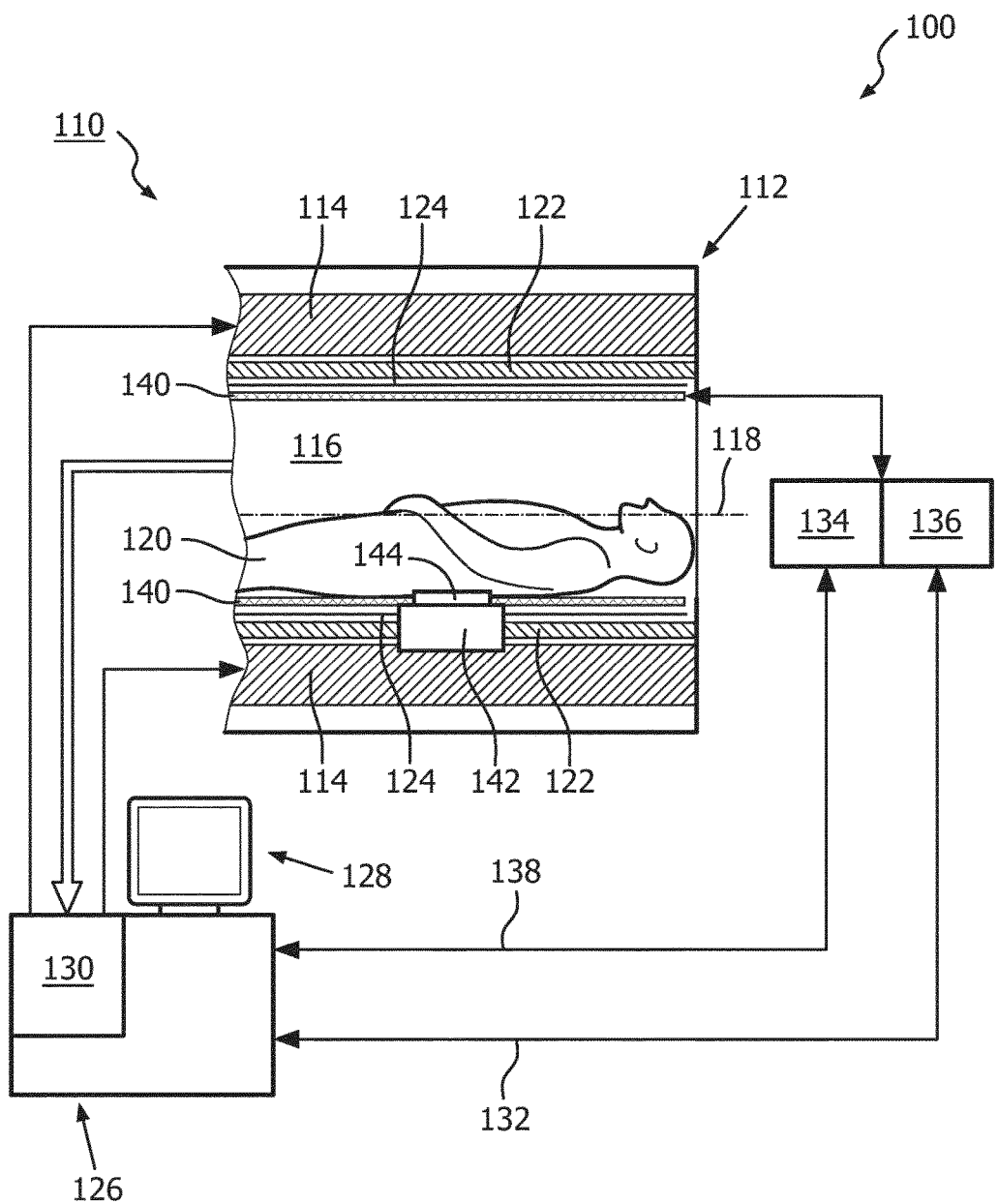
FIG. 1 is a schematic illustration of a first embodiment of a diagnostic imaging system in accordance with the invention.

FIG. 1 shows a schematic illustration of an embodiment of a diagnostic imaging system 100 comprising a magnetic resonance (MR) imaging system 110 and a hyperthermia device 111.

The MR imaging system 110 comprises an MR scanner 112 and includes a main magnet 114 provided for generating a static magnetic field. The main magnet 114 has a central bore that provides an examination space 116 around a center axis 118 for a subject of interest 120, usually a patient, to be positioned within. In this embodiment, the central bore and therefore the static magnetic field of the main magnet 114 has a horizontal orientation in accordance with the center axis 118. In an alternative embodiment, the orientation of the main magnet 114 can be different. Further, the MR imaging system 110 comprises a magnetic gradient coil system 122 provided for generating gradient magnetic fields superimposed to the static magnetic field. The magnetic gradient coil system 122 is concentrically arranged within the bore of the main magnet 114, as known in the art.

Further, the MR imaging system 110 includes a radio frequency (RF) antenna device 140 designed as a whole-body coil having a tubular body. The RF antenna device 140 is provided for applying an RF magnetic field to the examination space 116 during RF transmit phases to excite nuclei of the subject of interest 120. The RF antenna device 140 is also provided to receive MR signal from the excited nuclei during RF receive phases. In a state of operation of the MR imaging system 110, RF transmit phases and RF receive phases are taking place in a consecutive manner. The RF antenna device 140 is arranged concentrically within the bore of the main magnet 114. As is known in the art, a cylindrical metal RF screen 124 is arranged concentrically between the magnetic gradient coil system 122 and the RF antenna device 140.

Moreover, the MR imaging system 110 comprises an MR image reconstruction unit 130 provided for reconstructing MR images from the acquired MR signals and an MR imaging system control unit 126 with a monitor unit 128 provided to control functions of the MR scanner 112, as is commonly known in the art. Control lines 132 are installed between the MR imaging system control unit 126 and an RF transmitter unit 134 that is provided to feed RF power of an MR radio frequency to the RF antenna device 140 via an RF switching unit 136 during the RF transmit phases. The RF switching unit 136 in turn is also controlled by the MR imaging system control unit 126, and another control line 138 is installed between the MR imaging system control unit 126 and the RF switching unit 136 to serve that purpose. During RF receive phase, the RF switching unit 136 directs the MR signals from the RF antenna device 140 to the MR image reconstruction unit 130 after pre-amplification.

The hyperthermia device 111 is an ultrasonic irradiation device which is a high intensity focused ultrasound (HIFU) device for applying ultrasound to the target zone of the subject of interest, which is controlled to heat the target area with low intensity. The hyperthermia device 111 comprises a transducer box 142 including a transducer head, which is located integrally with the MR imaging system 110 to heat a subject of interest 120 located in the examination space 116, as shown in FIG. 1. The transducer head is movable to apply ultrasonic irradiation to a desired target zone of the subject of interest 120. A contact pad 144 is provided to improve the transmission of the ultrasonic irradiation from the transducer box 142 into the target zone.

Figure 3:
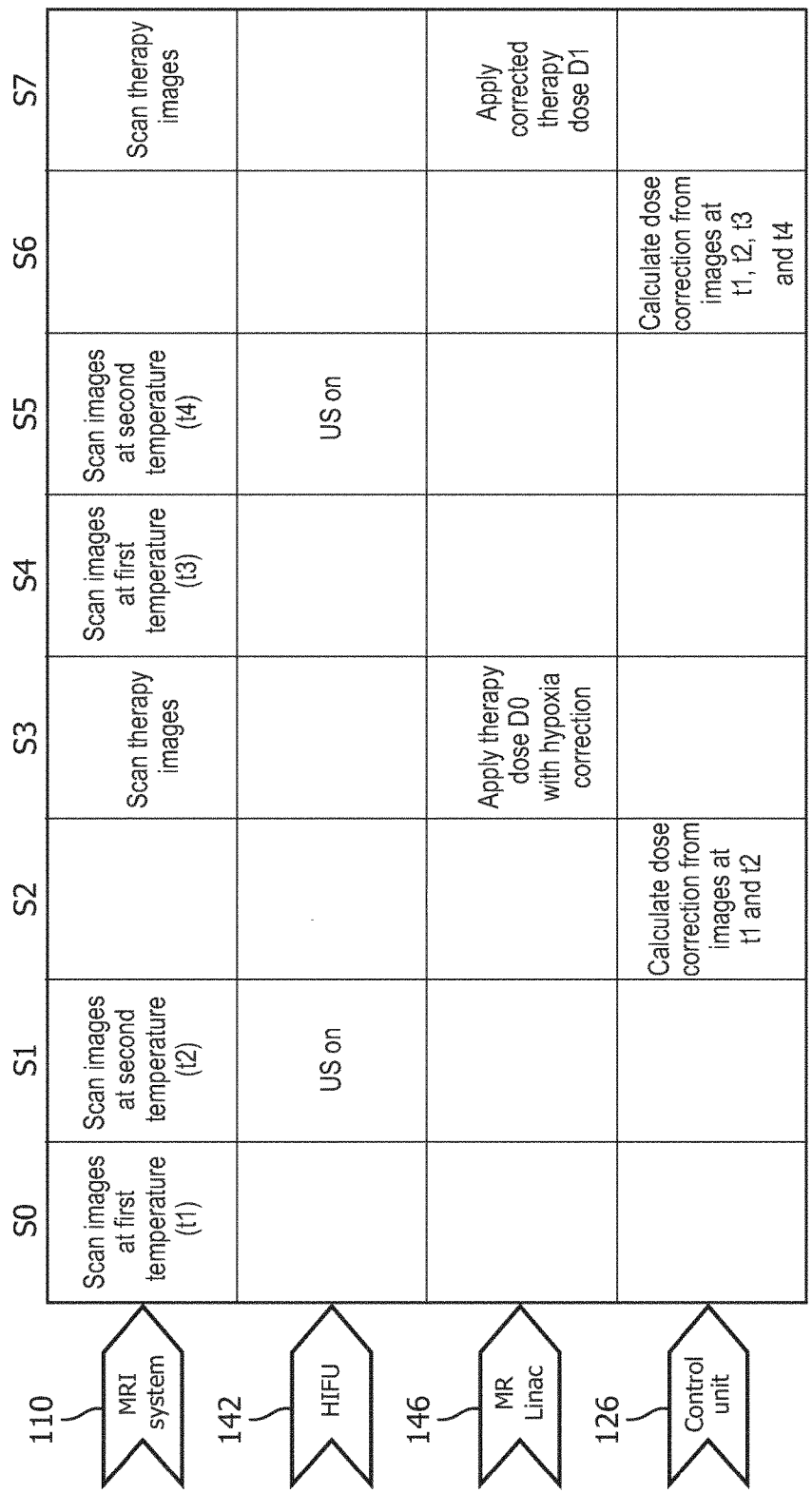
FIG. 3 is a timing diagram indicating the activation f different components of a treatment system.

A medical treatment system comprises the above diagnostic imaging system 100 and a treatment module 146 for applying a treatment to the subject of interest for destroying cells within the target zone. The treatment module 146, which is indicated in FIG. 3, is a high power linear accelerator (linac) for applying irradiation to the target zone of the subject of interest.

The control unit 126 for controlling the MRI system 110 performs a combined control of the MRI system 110, the hyperthermia device 111, and the treatment module 146.

The operation of the medical treatment system will now be described with reference to FIG. 3

In an initial step S0 at time t1, an image representation of a portion of a subject of interest 120 covering the target zone is provided by the MRI system 110. The subject of interest 120 has normal body temperature, also referred to as first temperature. The image representation is a blood oxygen level dependent (BOLD) image representation.

In a subsequent step at a time t2, the hyperthermia device 111 is activated by the control unit 126 to locally heat the target zone to a second temperature above the body temperature. When the second temperature is reached, the hyperthermia device 111 is de-activated and a further image representation of the portion of the subject of interest is provided by the MRI system 110. Also the further image representation is a BOLD image representation.

In step S2, the image representations obtained at the first and second temperatures are correlated by the control unit 126 to provide a diagnostic image representation of the portion of the subject of interest. The diagnostic image representation comprises information on temperature dependent changes of the metabolism of the subject of interest 120. In this embodiment, the diagnostic imaging system 100 is adapted to provide the diagnostic image representation including hypoxia information. The amount of hypoxia is estimated, and the amount of treatment damage to the cells is estimated.

Furthermore, the control unit 126 calculates a dose correction of an initial dose, which was applied prior to S0 to direct a treatment to such areas, where the cells have not yet been destroyed as desired. The dose correction is calculated based on the diagnostic image representation, i.e. based on the representations provided at t1 and t2. Accordingly, the hypoxia information is fed back to dose calculations to boost the dose on hypoxic volumes. Based on the damage estimation, the amount and location of dose is optimized to minimize damage to healthy tissue while ensuring the effectiveness of the treatment on the target zone during the irradiation. The dose refers to a location and intensity of the treatment applied by the treatment module. In this embodiment, the dose refers to a target area of the linac 146 and the intensity of the linac 146.

In step S3, the treatment is applied to the target zone by the linac 146 according to the dose calculated above. Furthermore, the MRI system 110 is operated to provide therapy images.

Subsequent steps S4 and S5 are essentially identical to steps S0 and S1, respectively, and provide image representations at times t3 and t4. Accordingly, at t3 an image representation at the first temperature is provided. Accordingly, the target area cools down to the first temperature, which is lower than the second temperature, by normal thermal conduction and perfusion. In an alternative embodiment, active cooling is applied to support cool down of the target area.

In step S6, the image representations obtained at the first and second temperatures at times t1, t2, t3 and t4 are correlated by the control unit 126 to provide a diagnostic image representation of the portion of the subject of interest 120 as described with respect to S2. With the correlation of multiple image representations for the first and second temperature, the process of the treatment is monitored. Again, based on the diagnostic image representation, the control unit 126 calculates a dose correction of the prior dose of S3.

In an alternative embodiment, the control module is further adapted to control the hyperthermia device 111 for locally heating the target zone within the portion of the subject of interest 120 together with the treatment module 146 for applying the treatment. Accordingly, the treatment is applied under hyperthermia conditions.

Figure 2:
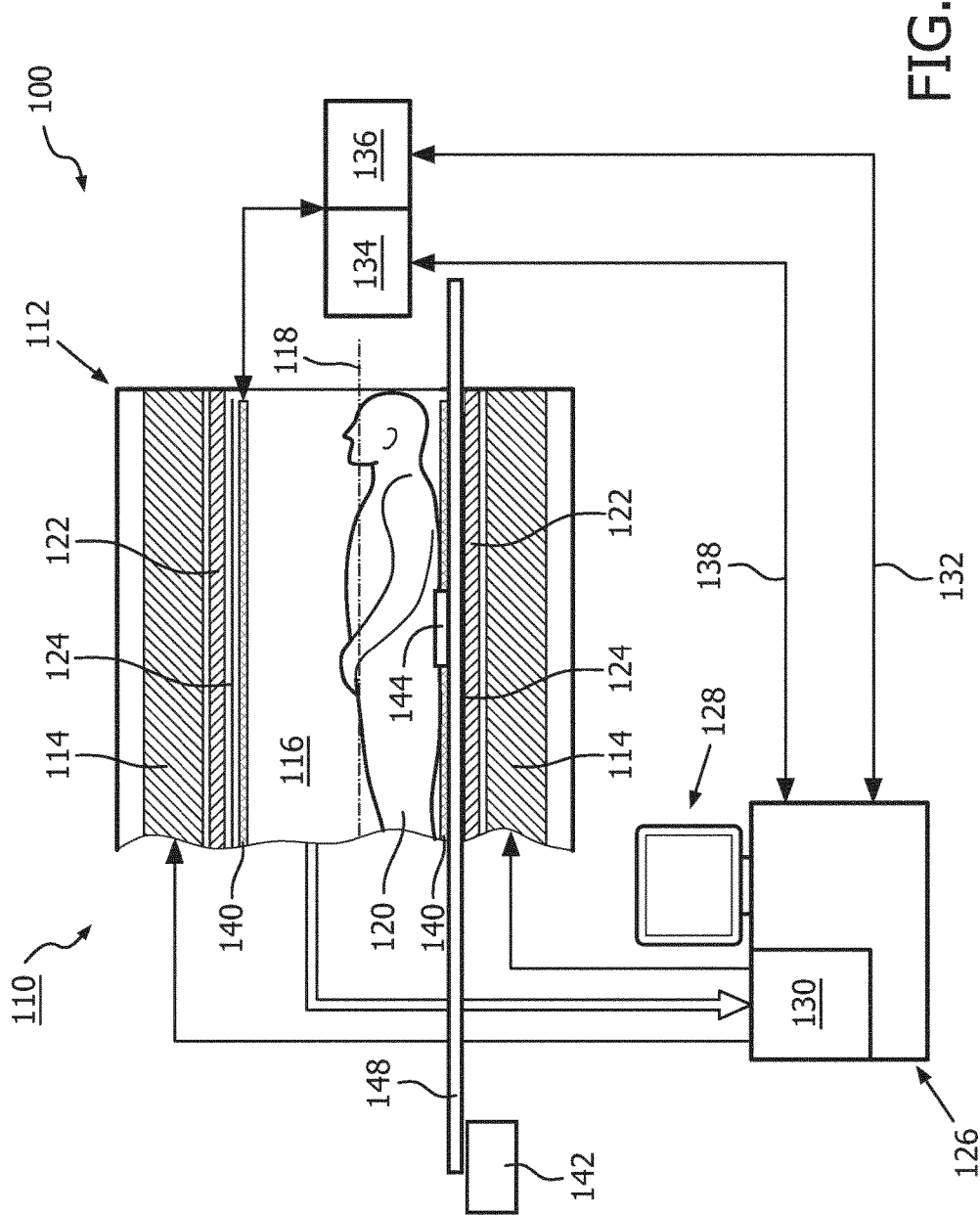
FIG. 2 is a schematic illustration of a second embodiment of a diagnostic imaging system in accordance with the invention.

FIG. 2 shows a schematic illustration of an embodiment of a diagnostic imaging system 100 according to a second embodiment. The diagnostic imaging system 100 according to the second embodiment is mostly identical to the diagnostic imaging system 100 according to the first embodiment, so that only differences will be described. Also the methods for providing a diagnostic image representation and for treatment are applied as described above.

The diagnostic imaging system 100 according to the second embodiment differs from the first embodiment merely in the positioning of the transducer box 142, which is positioned outside the examination space 116. Accordingly, to apply heating to the target zone, the subject of interest 120 is moved out of the examination space 116 on a movable tabletop 148. After heating the target zone, the subject of interest 120 is returned into the examination space 116.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 100 diagnostic imaging system
110 magnetic resonance (MR) imaging system
111 hyperthermia device
112 magnetic resonance (MR) scanner
114 main magnet
116 RF examination space
118 center axis
120 subject of interest
122 magnetic gradient coil system
124 RF screen
126 MR imaging system control unit
128 monitor unit
130 MR image reconstruction unit
132 control line
134 RF transmitter unit
136 RF switching unit
138 control line
140 radio frequency (RF) antenna device
142 transducer box
144 contact pad
146 treatment module, linac
148 tabletop

The invention claimed is:

1. An oncological treatment system comprising;
a magnetic resonance scanner configured to generate image representations of a portion of a subject to be treated, the image representations being indicative of hypoxia,
an ultrasound device configured to heat selectable areas of the portion of the subject,
a linear accelerator configured to irradiate selected locations in the portion of the subject with selected intensities,
one or more processors programmed to control the magnetic resonance scanner, the ultrasound device, and the linear accelerator to perform a pulsed operation of the ultrasound device and the magnetic resonance scanner to provide image representations of the portion of the subject of interest when the ultrasound device is inactive, including:
(a) controlling the magnetic resonance scanner to generate an initial image representation of the portion of the subject to be treated, the initial image representation being indicative of hypoxia,
(b) based on the initial image representation, selecting areas of the portion of the subject to be heated by the ultrasound device and locations in the portion of the subject to be irradiated and an irradiation intensity for each location,
(c) pulsing the ultrasound device to heat selected areas and controlling the linear accelerator to irradiate the selected locations with the selected intensities,
(d) when the ultrasound device is inactive, generating another image representation,
(e) based on a comparison of the initial and the another image representations, adjusting the selected areas of the portion of the subject to be heated by the ultrasound device, the locations irradiated by the linear accelerator, and the linear accelerator irradiation intensities,
(f) pulsing the ultrasound device to heat the adjusted selected areas and control the linear accelerator to irradiate the adjusted locations and/or with the adjusted intensities,
such that continuous verification of success and adaptation of the treatment is provided.

* * * * *